US00PP14634P29

(12) United States Plant Patent
Trees

(10) Patent No.: US PP14,634 P2
(45) Date of Patent: Mar. 23, 2004

(54) LANTANA PLANT NAMED 'BALUCGOLD'

(50) Latin Name: *Lantana camara*
Varietal Denomination: Balucgold

(75) Inventor: Scott C. Trees, Shell Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 17 days.

(21) Appl. No.: 10/329,803

(22) Filed: Dec. 26, 2002

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—Wood, Phillips, Katz, Clark & Mortimer

(57) ABSTRACT

A new and distinct Lantana plant named 'Balucgold', characterized by its dark yellow flowers, upright mounded growth habit, and dark green foliage.

1 Drawing Sheet

Latin name of genus and species of plant claimed: *Lantana camara.*
Variety denomination: 'Balucgold'.

BACKGROUND OF INVENTION

The present invention comprises a new and distinct Lantana plant, botanically known as *Lantana camara,* and hereinafter referred to by the cultivar name 'Balucgold'.

The new cultivar was developed by the inventor in a controlled breeding program during 1999, at Arroyo Grande, Calif. The objective of the breeding program was the development of Lantana cultivars with a well-branched, compact habit, continuous flowering and dark green foliage.

The female (seed) parent of 'Balucgold' was the commercially available Lantana variety 'Simon Yellow' (not patented), characterized by its yellow flowers and upright growth habit. The male (pollen) parent of 'Balucgold' was the commercially available Lantana variety 'Denholm White' (not patented), which exhibits a spreading habit and white flowers. 'Balucgold' was selected in May 2000 as a single flowering plant from within the progeny of the above stated cross and was initially designated '51-1'.

Asexual reproduction of the new cultivar at Arroyo Grande, Calif. and West Chicago, Ill. was carried out by the use of terminal stem cuttings has demonstrated that the new Lantana reproduces true to type with the characteristics of the new cultivar as herein described are firmly fixed and retained through successive generations of such asexual propagation.

SUMMARY OF INVENTION

It was found that the cultivar of the present invention:

(a) exhibits dark yellow colored flowers, (b) forms dark green foliage, and (c) exhibits an upright mounded growth habit.

The new cultivar of the present invention can be compared to its female parent, the commercially available Lantana variety, 'Simon Yellow'. In side-by-side comparison, plants of the new cultivar differ from plants of 'Simon Yellow'. It is found that the new cultivar has smaller leaves and flowers of a lighter yellow color than 'Simon Yellow'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 7 weeks in a greenhouse at West Chicago, Ill.

DETAILED BOTANICAL DESCRIPTION

Figure 1:
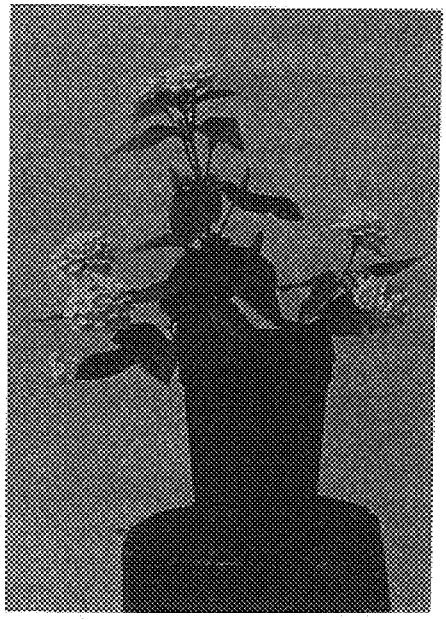
FIG. 1 illustrates the overall growth habit of the new cultivar.
Figure 2:
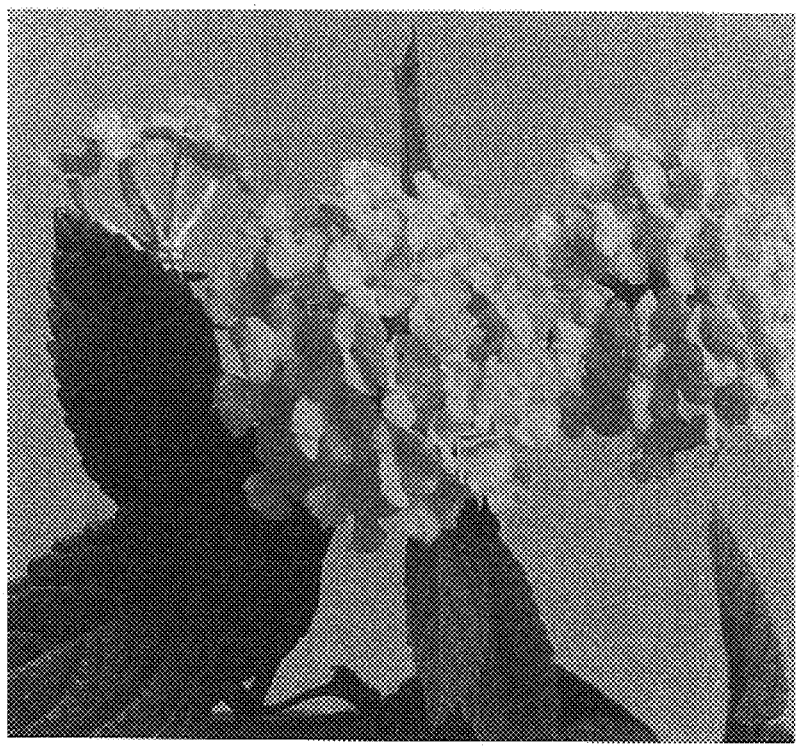
FIG. 2 illustrates a close up view of leaves and two inflorescences of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double poly-carbonate covered greenhouse under conditions comparable to those used in commercial practice. The plants were grown for 15 weeks while utilizing a soilless growth medium and maintaining temperatures of approximately 75° to 85° F. (24° to 29° C.) during the day and approximately 62° to 68° F. (17° to 20° C.) during the night and light levels of 4,000 to 10,000 footcandles.

Classification:
*Botanical.*—*Lantana camara* cultivar 'Balucgold'.
Parentage:
*Female parent.*—'Simon Yellow'.
*Male parent.*—'Denholm White'.
Propagation:
*Type cutting.*—Terminal tip.
*Time to initiate roots.*—Approximately 14 to 21 days.
*Root description.*—Fibrous, branching.

Plant description:

*Habit of growth.*—Moderately vigorous. Pinching improves branching. A mature plant, 7 weeks after the planting of a rooted cutting, measures approximately 16.3 cm in height and approximately 17 cm in width with 2.4 main branches.

*Form.*—Upright, mounded.

*Branch.*—Square, approximately 14 cm in length and 2 mm in diameter, with moderately pubescent with short stiff hairs. Color is 146B. Internode length at middle of stem is approximately 3 cm.

*Foliage.*—Leaves are opposite, ovate with serrate/crenate margin, acute apex and attenuate base. Upper and lower surface is densely covered with short, stiff hairs. Leaf length is approximately 6.7 cm and width is approximately 3.9 cm. Upper surface of mature foliage is 147A and lower surface is 147B. Upper and lower surfaces have pinnate-reticulate venation. Color of venation on upper surface is 144B. Color of venation on lower surface is 144D. Petiole surface is moderately covered with short, stiff hairs, length is approximately 1.2 cm, diameter is approximately 2 mm and color is 144B.

Flowering description:

*Flowering habit.*—Freely flowering.

*Natural flowering season.*—Year round in greenhouse environment and spring through autumn in outdoor garden.

Inflorescence description:

*Type.*—Terminal head.

*Shape.*—Spherical.

*Size.*—Approximately 2.2 cm in depth and approximately 3.6 cm in diameter with approximately 53.5 fully open flowers at any one time. Each flower is subtended by a single bract. Flowers are sessile.

*Bract.*—Shape: Lanceolate. Length: Approximately 6 mm. Width: Approximately 1 mm. Apex: Acute. Margin: entire. Texture: Lower surface is densely pubescent, upper surface is slightly pubescent with short hairs. Color: Both surfaces are 137A.

*Peduncle.*—Shape: Square. Length is approximately 3.8 cm and diameter is approximately 4 mm. Aspect: At acute angle to branch. Color: 146C Texture: Pubescent with short stiff hairs.

Flower description:

*Fragrance.*—Light.

*Shape.*—Round.

*Aspect.*—Concave.

*Lastingness of bloom.*—Approximately 6–9 days.

*Bud.*—Square, pillow shaped, approximately 3 mm in width and 2 mm in depth and 21A in color.

*Petals.*—Five, non overlaping,non-symetrical, fused at base forming corolla tube. Upper petal: Shape: Obovate. Apex: Broadly acute. Margin: Entire, undulate. Length from throat: Approximately 7 mm. Width: Approximately 8 mm. Lateral petals: Shape: Obovate. Apex: Obtuse. Margin: Entire, undulate. Length from throat: Approximately 4 mm. Width: Approximately 4 mm. Lower petals: Shape: Obovate. Apex: Obtuse. Margin: Entire, undulate. Length from throat: Approximately 7 mm. Width: Approximately 9 mm. Length: Approximately 7 mm. Width of upper petal: Approximately 8 mm. Width of lateral petals: Approximately 4 mm. Width of lower petal: Approximately 9 mm.

*Corolla.*—Diameter is approximately 1 cm. Petal color when fully open: the upper surface is 23A at margin, 24A in center. Color of lower surface is 23C. Upper and lower surfaces of petals are smooth and glabrous.

*Corolla tube.*—Length is approximately 1.3 cm, diameter at tube opening is approximately 1 mm, diameter at base is approximately 1 mm. Outside of tube is densely covered with short hairs. Color of outer surface: 24C with 10C at base. Inner surface of tube is smooth except for hairs around opening. Color of inner surface is 24D.

*Calyx.*—Tubular, formed by 5 fused sepals with acute tips. Length: Approximately 6 mm. Diameter: Approximately 1 mm. Color of both surface: 150D.

*Reproductive organs.*—There are 4 stamens fused to the corolla tube. The anther length is less than 1 mm and the color is 165B. Pollen is sparse and 18D in color. There is one pistil, 4 mm in length. The stigma shape is round, the length is less than 1 mm and the color is 2A. The style length is approximately 2 mm and the color is 2D. Ovary length is 1 mm and color is 144C.

Seed/fruit production: Seed/fruit production has not been observed.

Disease resistance: Resistance to pathogens has not been observed.

Hardiness zone: 'Balucgold' is hardy in zones nine (9) and above.

I claim:

1. A new and distinct cultivar of *Lantana camara* plant named 'Balucgold' substantially as herein shown and described, which:

(a) exhibits dark yellow colored flowers, (b) forms dark green foliage, and (c) exhibits an upright mounded growth habit.

* * * * *